United States Patent
Kiel et al.

(10) Patent No.: US 7,390,922 B2
(45) Date of Patent: Jun. 24, 2008

(54) PHENOLIC ACID SALTS OF GABAPENTIN IN LIQUID AND/OR SEMI-SOLID DOSAGE FORMS AND METHODS OF USE

(75) Inventors: Jeffrey S. Kiel, Gainesville, GA (US); H. Greg Thomas, Villa Rica, GA (US); Narasimhan Mani, Port Jefferson, NY (US)

(73) Assignee: Kiel Laboratories, Inc., Gainesville, GA (US)

( * ) Notice: Subject to any disclaimer, the term of this patent is extended or adjusted under 35 U.S.C. 154(b) by 338 days.

(21) Appl. No.: 10/806,260

(22) Filed: Mar. 22, 2004

(65) Prior Publication Data

US 2004/0192618 A1 Sep. 30, 2004

Related U.S. Application Data

(60) Provisional application No. 60/457,408, filed on Mar. 25, 2003.

(51) Int. Cl.
*C07C 229/28* (2006.01)

(52) U.S. Cl. ..................................... 562/507

(58) Field of Classification Search .................. None
See application file for complete search history.

(56) References Cited

U.S. PATENT DOCUMENTS

| | | | |
|---|---|---|---|
| 2,397,799 A | 4/1946 | Martin et al. | |
| 2,421,714 A | 6/1947 | Rieveschl | |
| 2,950,309 A | 8/1960 | Cavallito | |
| 3,282,789 A | 11/1966 | Marty et al. | |
| 4,024,175 A | 5/1977 | Satzinger et al. | |
| 4,309,989 A | 1/1982 | Fahim | |
| 4,552,899 A | 11/1985 | Sunshine et al. | |
| 4,619,934 A | 10/1986 | Sunshine et al. | |
| 4,749,697 A | 6/1988 | Sunshine et al. | |
| 4,749,711 A | 6/1988 | Sunshine et al. | |
| 4,749,721 A | 6/1988 | Sunshine et al. | |
| 4,749,722 A | 6/1988 | Sunshine et al. | |
| 4,749,723 A | 6/1988 | Sunshine et al. | |
| 4,767,402 A | 8/1988 | Kost et al. | |
| 4,839,354 A | 6/1989 | Sunshine et al. | |
| 5,025,019 A | 6/1991 | Sunshine et al. | |
| 5,068,413 A | 11/1991 | Steiner et al. | |
| 5,095,148 A | 3/1992 | Mettler et al. | |
| 5,132,451 A | 7/1992 | Jennings et al. | |
| 5,164,398 A | 11/1992 | Sims et al. | |
| 5,560,933 A | 10/1996 | Soon-Shiong et al. | |
| 5,599,846 A | 2/1997 | Chopdekar et al. | |
| 5,614,178 A | 3/1997 | Bloom et al. | |
| 5,624,938 A * | 4/1997 | Pernis | 514/313 |
| 5,663,415 A | 9/1997 | Chopdekar et al. | |
| 5,759,579 A | 6/1998 | Singh et al. | |
| 5,948,414 A | 9/1999 | Wiersma | |
| 6,037,358 A | 3/2000 | Gordziel | |
| 6,063,770 A | 5/2000 | Falcon | |
| 6,083,490 A | 7/2000 | Ellis et al. | |
| 6,117,452 A | 9/2000 | Ahlgren et al. | |
| 6,187,315 B1 | 2/2001 | Falcon | |
| 6,287,597 B1 | 9/2001 | Gordziel | |
| 6,306,904 B1 | 10/2001 | Gordziel | |
| 6,383,471 B1 * | 5/2002 | Chen et al. | 424/45 |
| 6,403,119 B2 | 6/2002 | Oppenheim et al. | |
| 6,417,206 B1 | 7/2002 | Leflein et al. | |
| 6,462,094 B1 | 10/2002 | Dang et al. | |
| 6,509,492 B1 | 1/2003 | Venkataraman | |
| 6,703,044 B1 | 3/2004 | Pinhasi et al. | |
| 6,740,312 B2 | 5/2004 | Chopin et al. | |
| 2004/0192616 A1 * | 9/2004 | Kiel et al. | 514/23 |
| 2004/0192617 A1 * | 9/2004 | Kiel et al. | 514/23 |

OTHER PUBLICATIONS

Cypress Pharmaceutical, Inc., "R-Tannic-S A/D," RX Only, Cypress Pharmaceutical, Inc., (Madison, MS), p. 1, 2 (Mar. 1, 2001).

DSC Laboratories, "Phenylephrine Tannate/Pyrilamine Tannate Suspension," RX Only, DSC Laboratories (Muskegon, MI), p. 1, 2 (Aug. 1, 2001).

Ronald Goldberg, M.D. and Franklin Shuman, M.D., "Evaluation of a Prolonged Action Oral Antihistaminic Preparation as Treatment for Allergic Disorders," Clinical Report, Clinical Medicine (Washington), vol. 72 (No. 9), pp. 1475-1479 (Sep. 1, 1965).

John Weiler, M.D. et al., "Randomized, double-blind, parallel groups, placebo-controlled study of efficacy and safety of Rynatan in the treatment of allergic rhinitis using an acute model," Annals of Allergy, ACAI (Iowa City, IA), vol. 64 (No. 1), p. 63-67 (Jan. 1, 1990).

Berge et al. Pharmaceutical Salts. Journal of Pharmaceutical Sciences, Jan. 1977, vol. 66, No. 1, pp. 1-19.

* cited by examiner

*Primary Examiner*—Yvonne Eyler
*Assistant Examiner*—Yevegeny Valenrod
(74) *Attorney, Agent, or Firm*—King & Schickli, PLLC

(57) ABSTRACT

The present invention relates to pharmaceutical compositions of gabapentin tannate, processes for production of those compositions and methods of use of those compositions. The present invention provides a novel process for preparation of the tannate salt of gabapentin in liquid or semi-solid dosage form for human and veterinary pharmaceutical use. Tannate salts of active pharmaceutical ingredients are used in sustained release applications and to improve certain organoleptic properties such as taste. The process may utilize either natural or synthetic tannic acid.

30 Claims, No Drawings

PHENOLIC ACID SALTS OF GABAPENTIN IN LIQUID AND/OR SEMI-SOLID DOSAGE FORMS AND METHODS OF USE

This application claims the benefit of U.S. Provisional Patent Application Ser. No. 60/457,408 filed on Mar. 25, 2003.

TECHNICAL FIELD

The present invention relates generally to the field of tannate chemistry and more specifically to liquid and/or semi-solid dosage forms of gabapentin tannate and related methods of use.

BACKGROUND OF THE INVENTION

The literature describes many ways of preparing gabapentin from a variety of starting materials, but there is no suggestion of the preparation of gabapentin tannate. U.S. Pat. No. 4,024,175 describes at least three methods of preparing gabapentin from cyclohexyl-1,1-diacetic acid. Each of these methods results in the formation of gabapentin hydrochloride salt, which may be converted to 1-(aminomethyl)-1-cyclohexaneacetic acid by treatment with a basic ion exchanger and then crystallized from a solvent such as ethanol/ether.

However, the prior art neither discloses nor suggests the preparation of gabapentin tannate and subsequent incorporation into suitable liquid and semi-solid dosage forms. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

SUMMARY OF THE INVENTION

In accordance with the purposes of the present invention, a process is provided for preparing a pharmaceutical composition for treating a condition of the central nervous system in a mammalian subject. That process comprises reacting gabapentin with tannic acid to produce a pharmaceutically effective amount of gabapentin tannate and processing the gabapentin tannate into suitable liquid and semi-solid dosage forms.

Naturally occurring tannic acid comprises a mixture of compounds. They are considered to be secondary metabolites, with a molecular weight of 500-5000 Da, that have no specific metabolic function. As with many natural polymers, a rigorous chemical definition of tannins is difficult.

Hydrolyzable tannins are molecules with a polyol (generally D-glucose) as a central core, with the hydroxyl groups of the carbohydrate partially or totally esterified with phenolic groups. They derive their name from their propensity to be hydrolyzed by mild acids or mild bases to yield carbohydrates and phenolic acids. Synthetic tannic acid may comprise a purified form of any of the components of naturally occurring tannic acid.

The present invention may utilize tannic acid of either a natural or synthetic source. The term "tannic acid" herein refers to either natural or synthetic tannic acid as described above.

The process may be further described as including providing one or more pharmaceutically acceptable excipients. The excipients may be selected from a group consisting of one or more thickening agents, one or more suspending agents, one or more sweetening agents, one or more flavoring agents, one or more preserving agents, one or more buffering agents, one or more anti-caking agents and mixtures thereof. Further, the process may be completed by means of in-situ conversion of gabapentin to gabapentin tannate.

In accordance with yet another aspect of the present invention, a process for preparing a pharmaceutical composition for treating a condition of the central nervous system in a mammalian subject may be described as including the steps of mixing tannic acid and a dispersing agent in a solvent to obtain a dispersion and adding gabapentin to that dispersion. More particularly, the process may include the dissolving of the gabapentin in a solvent before adding the gabapentin to the dispersion.

The dispersing agent may be provided in an amount equal to between about 0.05 to about 5.0% by weight of the dispersion. Additionally, the method includes the providing of the tannic acid in an amount equal to between about 0.05 to about 50.0% by weight of the dispersion. Further the method includes the step of providing the dispersing agent and the tannic acid in the composition at a weight ratio of between about 0.1:2 to about 100:1.

The gabapentin and the tannic acid may be provided in the composition at a weight ratio of between about 0.1:1 to about 100:1.

The process may include the selecting of one or more solvents from a group of solvents consisting of water, purified water, isopropyl alcohol, ethanol, glycerin, propylene glycol, mineral oil and mixtures thereof. Further, one or more pharmaceutically acceptable excipients may be added to the composition. The one or more dispersing agents and one or more excipients may be selected from a group consisting of magnesium aluminum silicate, xanthan gum, cellulose compounds, acacia, tragacanth, kaolin, pectin and mixtures thereof.

Still further, the process may include the adding of one or more sweetening agents to the composition. The one or more sweetening agents may be selected from a group consisting of sucrose, saccharin sodium, aspartame, sucralose and mixtures thereof. The sweetening agents may be provided in an amount equal to between about 0.05 to about 50.0% by weight of the total composition.

Still further, the process may include the step of adding one or more preservatives to the composition. The one or more preservatives may be selected from a group consisting of methylparaben, propylparaben, butylparaben and mixtures thereof. The preservatives may be provided in an amount equal to between about 0.05 to about 2.0% by weight of the total composition.

Still further, the process may include the maintaining of a pH of the reaction mixture at between about 2.0 to about 11.0 during processing.

Stated another way, the process may be described as comprising the steps of mixing one or more dispersing agents and tannic acid together to form a reaction mixture, adding gabapentin to that reaction mixture and adding one or more solvents to that reaction mixture.

The present invention also relates to a pharmaceutical composition for treating a condition of the central nervous system in a mammalian subject. That composition comprises as an active ingredient a pharmaceutically effective amount of gabapentin tannate. The composition may also include one or more pharmaceutical excipients.

The excipients may be selected from a group consisting of one or more dispersing agents, one or more anti-clumping agents, one or more thickening agents, one or more suspending agents, one or more sweetening agents, one or more flavoring agents, one or more preserving agents, one or more buffering agents, one or more anti-caking agents, one or more solvents and any mixtures thereof.

The one or more solvents may be selected from a group consisting of water, purified water, ethanol, isopropyl alcohol, glycerin, propylene glycol, mineral oil and mixtures thereof.

The one or more anti-caking agents, sweetening agents, preserving agents and anti-clumping agents may be selected from any of those previously noted in this document.

In accordance with yet another aspect of the present invention, a method is provided for treating a condition of the central nervous system in a mammalian subject. The method comprises administering a pharmaceutically effective amount of gabapentin tannate. The administration may be done orally. The method also includes the step of providing between about 0.1 to about 3600 mg of gabapentin in gabapentin tannate salt form.

DETAILED DESCRIPTION OF THE INVENTION

The present invention involves a novel method of synthesizing the tannate salt of the active pharmaceutical ingredient (API) gabapentin and subsequently processing the gabapentin tannate into liquid and semisolid pharmaceutical dosage forms. Gabapentin is a neuroleptic agent indicated as adjunctive therapy in the treatment of central nervous system conditions in mammalian subjects such as partial seizures, with and without secondary generalization, epilepsy, faintness attacks, hypokinesis, pain associated with shingles and cranial traumas. Gabapentin is a white to off-white crystalline solid and is a polymorphic substance. It is freely soluble in water and across a wide range of pH and is characterized by a marked bitter taste. Chemically, gabapentin is 1-(amino methyl) cyclohexaneacetic acid with the empirical formula $C_9H_{17}NO_2$ and a MW of 171.24. Typically, gabapentin is administered in multiple doses for optimal pharmacological action.

The literature describes many ways of preparing gabapentin from a variety of starting materials. U.S. Pat. No. 4,024,175 describes at least three methods of preparing gabapentin from cyclohexyl-1,1-diacetic acid. Each of these methods results in the formation of gabapentin hydrochloride salt, which may be converted to 1-(aminomethyl)-1-cyclohexaneacetic acid by treatment with a basic ion exchanger and then crystallized from a solvent such as ethanol/ether.

There is no mention or suggestion of preparing gabapentin tannate in the prior art. Further, there is no suggestion of liquid or semi-solid pharmaceutical dosage forms containing gabapentin tannate. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

Gabapentin is structurally related to the neurotransmitter γ-aminobutyric acid (GABA) but unlike GABA, is able to cross the blood-brain barrier. Although its exact mechanism of action remains unclear, gabapentin was recently shown to be a selective agonist at the gb1a-gb² heterodimer and postsynaptic $GABA_B$ receptor, a newly identified receptor subtype. The pharmacokinetics of gabapentin have been well characterized in adults. Peak plasma gabapentin concentrations occur 2-3 hours post-dose. The absolute bioavailability of gabapentin is approximately 60% after administration of 300 mg and is dose-dependent. While steady-state plasma gabapentin concentrations increased with increasing doses, the increase is not proportional to dose possibly due to saturation of the active transport across the gut via the L-amino acid transporter. Gabapentin does not bind to plasma proteins and is not metabolized. Gabapentin is eliminated via glomerular filtration, and dosage adjustment is necessary in patients with renal impairment. In subjects with normal renal function, gabapentin elimination half-life averages between 5 and 7 h. Dosing recommendations are 900-1800 mg/day for anticonvulsant activity and panic disorders may require dosages in the range of between about 3000 to 3600 mg/day of gabapentin. The bioavailability and high dosage requirements for pharmacological action stipulate multiple dosings of gabapentin.

Naturally occurring tannic acid comprises a mixture of compounds. They are considered to be secondary metabolites, with a molecular weight of 500-5000 Da, that have no specific metabolic function. They are complex phenol-rich polymers found in many foods. As with many natural polymers, a rigorous chemical definition of tannins is difficult. In general two classes are distinguished—the hydrolyzable and the condensed tannins. Hydrolyzable tannins or tannic acids are referenced in the various pharmacopeias and are composed of gallic acid or its condensation product ellagic acid esterified to the hydroxyl groups of glucose.

Hydrolyzable tannins are molecules with a polyol (generally D-glucose) as a central core, with the hydroxyl groups of the carbohydrate partially or totally esterified with phenolic groups. They derive their name from their propensity to be hydrolyzed by mild acids or mild bases to yield carbohydrates and phenolic acids. Synthetic tannic acid may comprise a purified form of any of the components of naturally occurring tannic acid.

The present invention may utilize tannic acid of either a natural or synthetic source. The term "tannic acid" herein refers to either natural or synthetic tannic acid as described above.

Tannic acid elicits a characteristic astringent taste. A pH independent decrease in measures of amiloride-sensitive sodium channels in the tongue, which are regarded as conveying salty taste, has been observed when tannic acid was applied to the lingual surface. Physiologically, it has been demonstrated that there is a pH independent inhibition of chorda tympani responses to bitter and salty stimuli in the presence of tannic acid. The above mechanism of action has been used to explain experimental results which showed a taste suppression of 100% by tannic acid, of compounds like quinine HCl, papaverine HCl (bitter tasting compounds), NaCl (salty) and tartaric acid (sour). These properties explain why tannate salts of the active ingredients also possess better organoleptic properties, such as taste.

The formation of the tannate salt is by the reaction of the amine groups (in the 1°, 2°, 3°, 4° or amphoteric configuration) or of other basic functional groups with the carboxylic and hydroxyl groups present in tannic acid. For example, the amine groups of the API could react covalently with the hydroxyl groups of tannic acid by an oxime formation or by the ionization of the tannic acid and the protonation of the nitrogen atom in the amine group to form an ionic bond, to generate the tannate salt. In the present invention the active ingredient gabapentin is present in zwitter-ionic form. The protonated nitrogen reacts with tannic acid to form the tannate salt. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

The ratio of the gabapentin to tannic acid has a marked effect on the yield of the reaction to form the tannate salt. Typically, tannic acid needs to be present in a concentration of at least one half to five-fold that of the API by weight. The dispersing or anti-clumping agents used are naturally occurring gums or other polymers used as thickening agents. The amount and ratio of dispersing or anti-clumping agent and tannic acid, required for the completion of the reaction, is determined by the concentration of the gabapentin. The dispersing or anti-clumping agent serves as an adherent or a solid support for the tannic acid molecules to facilitate the reaction between the gabapentin and tannic acid. In addition it also prevents the clumping and aggregation of the tannate salt formed, which aids in the uniform distribution of the precipitate in the mixture. The synthetic process can be used as a conversion method for generating tannate salts of gabapentin and is a novel way of directly incorporating them into suitable liquid dosage forms.

In the dispersion method, the gabapentin tannate salt obtained from the conversion process can be transferred directly to a suitable liquid medium, which comprises co-solvents, preservatives, sweetening/flavoring, pH adjusting, coloring, thickening and anti-caking agents. The resulting mixture can be processed into suspensions and other suitable liquid dosage forms.

By starting with a commonly available form of the gabapentin, which is converted to a tannate salt, the invention provides an efficient and reproducible method to manufacture products containing gabapentin tannate salts as active ingredients. The complex thus obtained can be further incorporated into liquid or semi-solid dosage forms for pharmaceutical use.

The compositions of the present invention may be prepared for oral administration in the form of elixirs, syrups and the preferred forms of suspensions formulated so that ideally each 5 ml (approximately 1 teaspoon) of suspension would contain approximately 0.1 to 3600 mg of gabapentin in the tannate salt form, at a pH range of 2.0-11.0.

Suspensions of the compositions of the present invention may be prepared, such that each 5 ml (one teaspoon) contains 900 mg of gabapentin tannate, preferably by reacting the aqueous solution or the powder form of the drug with a tannic acid mixture in liquid or powder form, without the use of volatile solvents. The tannate salt prepared can then be directly incorporated into suitable pharmaceutically effective dosage forms without further purification and isolation. The suspension formulations may additionally contain one or more of the following: sodium benzoate, coloring, natural and artificial flavors, xanthan gum, magnesium aluminum silicate, methyl paraben, purified water, saccharin, sodium hydroxide, tannic acid and sucrose or sorbitol. Example 1, which is illustrative of a typical suspension formulation of the present invention, is prepared as follows:

EXAMPLE 1

| Ingredient | Milligrams per 5 ml |
|---|---|
| Gabapentin Tannate | 900.0 |
| Xanthan gum | 27.5 |
| Magnesium Aluminum Silicate | 40.0 |
| Sodium Benzoate | 5.0 |
| Methylparaben | 10.0 |
| Sucrose | 50.0 |
| Saccharin Sodium | 5.0 |
| Glycerin | 375.0 |
| Artificial Strawberry Flavor | 15.0 |
| FD&C Red #40 | 3.0 |
| Purified Water, USP (Deionized) | adjust to 5 ml |

The conversion process used in this example to synthesize the tannate salt of gabapentin is done using the following procedure at room temperature: About 150 ml of purified water is placed in a suitable vessel and gabapentin is added to the water and stirred to form a solution. 500 ml of purified water is placed in a suitable container and mixed. While mixing the water, the magnesium aluminum silicate is added in small portions. Subsequently, tannic acid is added and mixing is continued to form a dispersion. While mixing the tannic acid dispersion, the solution of gabapentin is added slowly to obtain the gabapentin tannate salt.

The saccharin sodium, sucrose, xanthan gum and a part of the MAS are dispersed in purified water, using a suitable mixer. The coloring agent and the artificial strawberry flavor are then added and mixing is continued to generate the suspending medium.

The gabapentin tannate as prepared is transferred to the suspending medium and mixing is continued to disperse the tannate salt. The sodium benzoate and methylparaben are then dispersed in the glycerin and added to the suspending medium containing the active and mixed to get a uniform dispersion. Finally, purified water is added to make up to the suspension to the required volume and mixed to obtain an elegant product.

Tannic acid may also be used for pH adjustment. Monobasic sodium phosphate, USP, and Dibasic sodium phosphate, USP, Anhydrous may also be included in the formula for pH adjustment.

EXAMPLE 2

| Ingredient | Milligrams per 5 ml |
|---|---|
| Gabapentin Tannate | 550.000 |
| Saccharin Sodium, USP | 2.529 |
| Sucrose, NF | 500.00 |
| Glycerin, USP | 376.47 |
| Magnesium Aluminum Silicate, NF | 88.24 |
| Kaolin, USP | 80.59 |
| Pectin, USP | 88.24 |
| Methylparaben, NF | 10.00 |
| Benzoic Acid, USP | 5.00 |
| FD&C Red #40 | 0.76 |
| FD&C Blue #1 | 0.21 |
| Grape Flavor | 10.00 |
| Purified Water, USP | qs to volume |
| Total (ml) | 5.000 |

The conversion process used in this example to synthesize the tannate salt of gabapentin is done using the following procedure at room temperature: 500 ml of purified water is placed in a suitable container and mixed. While mixing the water, the magnesium aluminum silicate is added in small portions. Subsequently, tannic acid is added and mixing is continued to form a dispersion. While mixing the tannic acid dispersion, gabapentin powder is added slowly to obtain gabapentin tannate salt.

The saccharin sodium, sucrose, kaolin and a part of the MAS are dispersed in purified water in a stainless steel mixing tank, using a suitable mixer. The coloring agent and the artificial grape flavor are then added and mixing is continued to generate the suspending medium.

The gabapentin tannate prepared as described is transferred to the suspending medium and mixing is continued to disperse the tannate salt. The pectin is dispersed in glycerin in a mixing tank using a mixer. The benzoic acid and methylparaben are then dispersed in the glycerin mixture in the tank. The glycerin mixture is added to the suspending medium containing the active ingredients and mixed to get a uniform dispersion. Finally, purified water is added to make up the suspension to the required volume and mixed to obtain an elegant product.

The dosage administered will be dependent on the age, health and weight of the recipient, kinds of concurrent treatment, if any, frequency of treatment and desired effect.

It should be understood that the above examples are only illustrative of the invention disclosed herein. Given the present disclosure, it is anticipated that numerous variations will occur to those skilled in the art without departing from the spirit and scope of the present invention. For example, while compositions of gabapentin tannate for oral administration have been described, it should be appreciated that like compositions could also be prepared for nasal and intravenous administration if desired. A latitude of modification, substitution and change is intended and in some instances, some features of the invention may be employed without a corresponding use of other features. Accordingly, it is intended that the spirit and scope of the invention disclosed herein should be limited only by the following claims.

What is claimed is:

1. A process for preparing gabapentin tannate to be used in a pharmaceutical composition, said process comprising: reacting gabapentin with tannic acid.

2. The process of claim 1 including selecting said tannic acid from either natural or synthetic origin.

3. The process of claim 1 including providing one or more pharmaceutically acceptable excipients.

4. The process of claim 1 including providing gabapentin tannate in liquid or semi-solid dosage forms.

5. The process of claim 1 including providing gabapentin tannate in suspension dosage form.

6. A process for preparing gabapentin tannate to be used in a pharmaceutical composition, said process comprising:
mixing tannic acid and a dispersing agent in a solvent to obtain a dispersion; and
adding gabapentin to the said dispersion.

7. The process of claim 6 including dissolving said gabapentin in a solvent before adding said gabapentin to said dispersion.

8. The process of claim 6, including providing said dispersing agent in an amount equal to between about 0.05 to about 5.0% by weight of said dispersion.

9. The process of claim 6, including providing said tannic acid in an amount equal to between about 0.05 to about 50.0% by weight of said dispersion.

10. The process of claim 6, including providing said dispersing agent and said tannic acid in said composition at a weight ratio of between about 0.1:2 to about 100:1.

11. The process of claim 6, including providing said gabapentin and said tannic acid in said composition at a weight ratio of between about 0.1:1 to about 100:1.

12. The process of claim 6, including selecting said solvent from a group of solvents consisting of water, purified water, isopropyl alcohol, ethanol, glycerin, propylene glycol, mineral oil and mixtures thereof.

13. The process of claim 6, further including adding one or more pharmaceutically acceptable excipients to said composition and selecting said dispersing agent and said excipients from a group consisting of magnesium aluminum silicate, xantban gum, cellulose compounds, acacia, tragacanth, kaolin, pectin and mixtures thereof.

14. The process of claim 6, further including adding one or more sweetening agents to said composition, and selecting said sweetening agents from a group consisting of sucrose, saccharin sodium, aspartame, sucralose and mixtures thereof.

15. The process of claim 14, including providing said sweetening agent in an amount equal to between about 5.0 to about 50.0% by weight of said composition.

16. The process of claim 6, including adding one or more preservatives to said composition and selecting said preservatives from a group consisting of methylparaben, propylparaben, butylparaben and mixtures thereof.

17. The process of claim 16, including providing said preservative in an amount equal to between about 0.05 to about 2.0% by weight of said composition.

18. The process of claim 6, including maintaining a pH of between about 2.0 to about 11.0 during said process.

19. The process of claim 6, including adding one or more excipients to said composition and selecting said excipients from a group consisting of a thickening agent, a suspending agent, a sweetening agent, a flavoring agent, a preserving agent, a buffering agent, an anti-caking agent and mixtures thereof.

20. A composition comprising gabapentin tannate.

21. The composition of claim 20 further including one or more pharmaceutical excipients.

22. The composition of claim 21, wherein said excipients are selected from a group consisting of a dispersing agent, an anti-clumping agent, a thickening agent, a suspending agent, a sweetening agent, a flavoring agent, a preserving agent, a buffering agent, an anti-caking agent, a solvent and any mixtures thereof.

23. The composition of claim 21, wherein said composition further includes one or more solvents selected from a group consisting of water, purified water, ethanol, isopropyl alcohol, glycerin, propylene glycol mineral oil and mixtures thereof.

24. The composition of claim 21, wherein said composition further includes one or more anti-caking agents selected from a group consisting of magnesium aluminum silicate, xanthan gum, cellulose compounds, acacia, tragacanth, kaolin, pectin and mixtures thereof.

25. The composition of claim 21, wherein said composition further includes one or more sweetening agents selected from a group consisting of sucrose, saccharin sodium, aspartame, sucralose and mixtures thereof.

26. The composition of claim 21, wherein said composition further includes one or more preserving agents selected from a group consisting of methylparaben, propylparaben, butylparaben and mixtures thereof.

27. The composition of claim 21, wherein said composition further includes one or more anti-clumping agents selected from a group consisting of magnesium aluminum silicate xanthan gum, polyvinylpyrrolidone, cellulose compounds, magnesium stearate, colloidal silica, talc, stearic acid, calcium stearate, lactose, mannitol, sucrose and mixtures thereof.

28. The composition of claim 20, wherein said composition is in a liquid or semi-solid dosage form.

29. The composition of claim 20, wherein said composition is in suspension form.

30. A process for preparing gabapentin tannate to be used in a pharmaceutical composition, said process comprising:
   (i) reacting gabapentin with tannic acid to produce gabapentin tannate; and
   (ii) directly incorporating the gabapentin tannate into a suitable pharmaceutical suspension dosage form without further purification and isolation.

* * * * *